US012805721B2

(12) United States Patent
Ge et al.

(10) Patent No.: US 12,805,721 B2
(45) Date of Patent: Nov. 24, 2026

(54) FUNDUS IMAGE ANALYSIS SYSTEM

(71) Applicant: Eyetelligence Pty Ltd, Melbourne (AU)

(72) Inventors: Zongyuan Ge, Chadstone (AU); Mingguang He, Chadstone (AU); Zhihong Lin, Chadstone (AU); Wei Meng, Chadstone (AU); Danli Shi, Chadstone (AU)

(73) Assignee: Eyetelligence Pty Ltd, Melbourne (AU)

( * ) Notice: Subject to any disclaimer, the term of this patent is extended or adjusted under 35 U.S.C. 154(b) by 148 days.

(21) Appl. No.: 18/875,720

(22) PCT Filed: Jun. 16, 2023

(86) PCT No.: PCT/AU2023/050535
§ 371 (c)(1),
(2) Date: Dec. 16, 2024

(87) PCT Pub. No.: WO2023/240319
PCT Pub. Date: Dec. 21, 2023

(65) Prior Publication Data
US 2026/0013719 A1 Jan. 15, 2026

(30) Foreign Application Priority Data
Jun. 16, 2022 (AU) ................................ 2022901641

(51) Int. Cl.
*A61B 3/12* (2006.01)
*A61B 3/00* (2006.01)
(Continued)

(52) U.S. Cl.
CPC .............. *A61B 3/12* (2013.01); *A61B 3/0025* (2013.01); *A61B 3/1005* (2013.01); (Continued)

(58) Field of Classification Search
CPC ....... A61B 3/12; A61B 3/0025; A61B 3/1005; G06T 7/11; G06T 7/0012;
(Continued)

(56) References Cited

U.S. PATENT DOCUMENTS

2019/0014982 A1* 1/2019 Bhuiyan .................. G06T 7/44
2024/0415386 A1* 12/2024 Gil ......................... A61B 3/103

FOREIGN PATENT DOCUMENTS

CN 112001928 A 11/2020
CN 113269737 A 8/2021
(Continued)

OTHER PUBLICATIONS

Shi, et al.; A Deep Learning System for Fully Automated Retinal Vessel Measurement in High Throughput Image Analysis; Frontiers in Cardiovascular Medicine; 2022.
(Continued)

*Primary Examiner* — David F Dunphy
(74) *Attorney, Agent, or Firm* — Dickinson Wright PLLC; Andrew D. Dorisio

(57) ABSTRACT

Described herein is a fundus image analysis system including a pre-segmentation image quality assessment module for receiving a fundus input image, and performing overall retinal image quality assessment and measurement quality assessment on the fundus input image; segmentation module for segmenting retinal vessel, artery, vein and optic disc to produce segmentation maps from the fundus input image; and a measurement module for computing region specific measurements within a standard zone within the fundus input image, and global physical or geometric measures of the whole fundus input image.

20 Claims, 5 Drawing Sheets

(51) Int. Cl.

*A61B 3/10* (2006.01)
*G06T 7/00* (2017.01)
*G06T 7/11* (2017.01)

(52) U.S. Cl.

CPC .............. *G06T 7/0012* (2013.01); *G06T 7/11* (2017.01); *G06T 2207/20084* (2013.01); *G06T 2207/30041* (2013.01); *G06T 2207/30101* (2013.01); *G06T 2207/30168* (2013.01)

(58) Field of Classification Search

CPC . G06T 2207/20084; G06T 2207/30041; G06T 2207/30101; G06T 2207/30168

See application file for complete search history.

(56) References Cited

FOREIGN PATENT DOCUMENTS

| | | | | |
|---|---|---|---|---|
| CN | 118015058 A * | 5/2024 | ............... | G06T 7/60 |
| WO | 2021169128 A1 | 9/2021 | | |

OTHER PUBLICATIONS

Martinez-Perez, et al.; Retinal Vascular Tree Morphology: A semi-automatic quantification; IEEE; 2023.

* cited by examiner

FUNDUS IMAGE ANALYSIS SYSTEM

FIELD

The present invention relates generally to systems and methods for analysing fundus images, and in particular to the use of such systems and methods for automatically qualifying retinal vessels to inform an assessment of micro-vascular heath. The invention has application, for example, in a retina-based microvascular health assessment system.

BACKGROUND

Retinal vessels mirror the microvascular state of the body. Changes in vascular morphology have been reported to be associated with a wide range of ocular or systemic diseases, including life-threatening cardiovascular disease. Despite many studies examining the association of retinal vessel and vascular disease risks, these investigations are very much limited by the reliable and efficient measures of retinal vessel profile.

Analysis of retinal imaging includes two main tasks, namely classification and detection. The difficulty of the tasks is emphasised by the complexity of the visualised features in particular because the image presents a projection of several layers of soft tissues.

A series of machine learning (ML) methods and software tools have been developed for the quantitative assessment of the retinal vasculature, but they are often time-consuming and require significant manual assistance. Other limitations of existing methods and tools include small measurement areas and having limited measurement parameters.

Deep learning (DL) methods have been established in recent years for different medical-imaging-related task including retinal image processing. DL methods have out-performed other ML methods in achieving retinal vessel segmentation with quicker processing time and accuracy. However, the size and complexity of the imaging makes the application of state-of-the-art DL methods less straightfor-ward, both in training and complexity.

Although existing DL-based methods have reported rea-sonably good accuracy, further improvements are required for effective adoption in real-world scenarios. These meth-ods must account for substantial variations in image quality, resolution, fundus camera types, and pathological lesions. A further technical challenge in vessel segmentation is broken vessels and misclassification of arteries and veins, especially at the complex branching or crossing points.

It would be desirable to provide a fundus image analysis system that facilitates fast, reliable, and detailed retinal vessel quantification. It would also be desirable to provide a fundus image analysis system that ameliorates or overcomes one or more problems or inconveniences of known fundus image analysis systems.

SUMMARY

In accordance with an aspect of the invention, there is provided a fundus image analysis system including:

- a pre-segmentation image quality assessment module for receiving a fundus input image, and
  - performing overall retinal image quality assessment and measurement quality assessment on the fundus input image;
- a segmentation module for segmenting retinal vessel, artery, vein and optic disc to produce segmentation maps from the fundus input image; and

- a measurement module for computing
  - region specific measurements within a standard zone within the fundus input image, and
  - global physical or geometric measures of the whole fundus input image.

Preferably, the segmentation module has a four stacked light-weight U-Net architecture, with a retinal vessel seg-mentation root and artery, vein and optical disc segmentation branches.

In one or more embodiments, the retinal vessel map generated by the retinal vessel segmentation root is used to guide subsequent artery, vein and optical disc segmentation.

In one or more embodiments, the retinal vessel segmen-tation root
- receives a fundus input image and
- generates a vessel segmentation map; and the artery, vein and optical disc segmentation branches
- receive the vessel segmentation map,
- concatenate the vessel segmentation map to the fundus input image and
- simultaneously generate artery, vein and optic disc seg-mentations from the concatenated vessel segmentation map and fundus input image.

The fundus image analysis system may further include:
- a post-segmentation image quality assessment module for excluding selected images from subsequent measure-ment.

In one or more embodiments, selected images are excluded on any one or more of the following criteria: no detectable optic disc; less than six arteries and six veins detectable in the standard zone; or less than two arteries and two veins detected in the whole fundus input image.

In one or more embodiments, the measurement module computes region specific measurements within a standard zone of 0.5-1.0 disc diameters away from an optic disc margin within the fundus input image.

In one or more embodiments, the measurement module measures a central retinal artery equivalent (CRAE) and central retinal vein equivalent (CRVE) from largest arteries and veins detected in the standard zone.

In one or more embodiments, the measurement module also computes hierarchical orders to enable subsequent stratification. Orders may be assigned for each segment, Strahler order and vessel.

In one or more embodiments, the measurement module converts vessels into segments separated by interruptions at the branching or crossing points, and measures one or more of diameter, arc length, chord length, length diameter ratio (LDR), tortuosity, branching angle (BA), branching angle from edges (BA_edge), branching coefficient (BC), angular asymmetry (AA), asymmetry ratio (AR), junctional expo-nent deviation (JED), and fractal dimension (FD) of the segments.

In accordance with an aspect of the invention, there is provided a method of analysing a fundus image including the steps of:

- at a pre-segmentation image quality assessment module,
  - receiving a fundus input image, and
  - performing overall retinal image quality assessment and measurement quality assessment on the fundus input image;
- at a segmentation module, segmenting retinal vessel, artery, vein and optic disc to produce segmentation maps from the fundus input image; and
- at a measurement module, computing
  - region specific measurements within a standard zone within the fundus input image, and global physical or geometric measures of the whole fundus input image.

In one or more embodiments, the segmentation module has a four stacked light-weight U-Net architecture, with a retinal vessel segmentation root and artery, vein and optical disc segmentation branches.

In one or more embodiments, the method further includes the step of using the retinal vessel map generated by the retinal vessel segmentation root to guide subsequent artery, vein and optical disc segmentation.

In one or more embodiments, the retinal vessel segmentation root receives a fundus input image and generates a vessel segmentation map; and the artery, vein and optical disc segmentation branches receive the vessel segmentation map, concatenate the vessel segmentation map to the fundus input image and simultaneously generate artery, vein and optic disc segmentations from the concatenated vessel segmentation map and fundus input image.

In one or more embodiments, the method further includes:

at a post-segmentation image quality assessment module, excluding selected images from subsequent measurement.

In one or more embodiments, the method further includes:

excluding the selected images on any one or more of the following criteria: no detectable optic disc; less than six arteries and six veins detectable in the standard zone; or less than two arteries and two veins detected in the whole fundus input image.

In one or more embodiments, the method further includes:

at the measurement module, computing region specific measurements within a standard zone of 0.5-1.0 disc diameters away from an optic disc margin within the fundus input image.

In one or more embodiments, the method further includes:

at the measurement module, measuring a central retinal artery equivalent (CRAE) and central retinal vein equivalent (CRVE) from largest arteries and veins detected in the standard zone.

A method according to any one of claims 12 to 19, and further including, at the measurement module, computing hierarchical orders to enable subsequent stratification.

In one or more embodiments, the orders are assigned for each segment, Strahler order and vessel.

In one or more embodiments, the method further includes, at the measurement module, converting vessels into segments separated by interruptions at the branching or crossing points, and measuring one or more of diameter, arc length, chord length, length diameter ratio (LDR), tortuosity, branching angle (BA), branching angle from edges (BA_edge), branching coefficient (BC), angular asymmetry (AA), asymmetry ratio (AR), junctional exponent deviation (JED), and fractal dimension (FD) of the segments.

BRIEF DESCRIPTION OF THE DRAWINGS

The invention will now be described, by way of example only, with reference to the accompanying drawings, in which.

DETAILED DESCRIPTION

Fundus Image Analysis System

Figure 1:
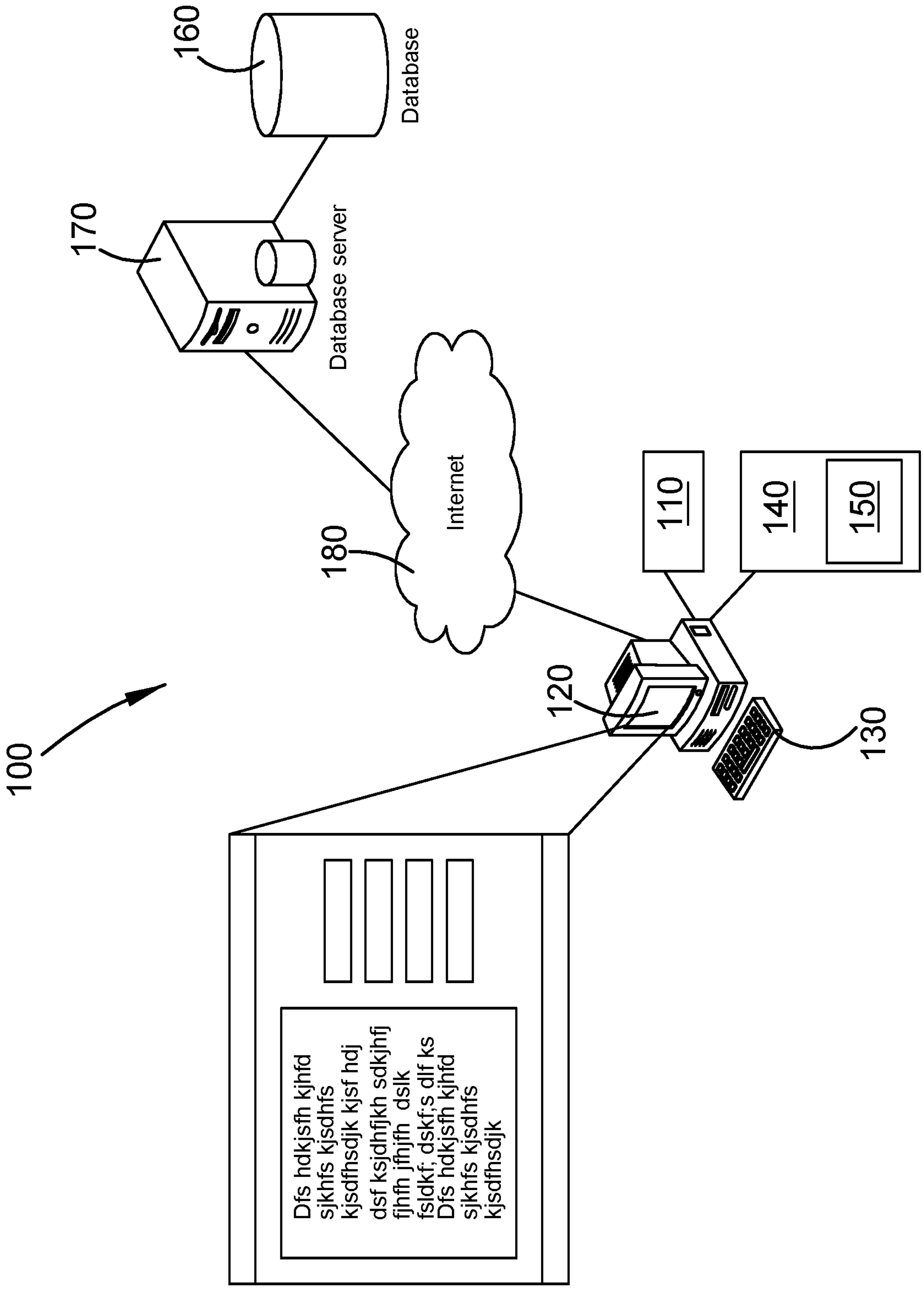
FIG. 1 is a schematic diagram of a fundus image analysis system according to one or more embodiments of the present invention.

Referring to FIG. 1, there is shown a fundus image analysis system 100 in accordance with embodiments of the present invention. The system 100 includes a processor 110 coupled to be in communication with an output device 120 in the form of a display according to preferred embodiments of the present invention. The system 100 includes one or more input devices 130, such as a mouse and/or a keyboard and/or a pointer, coupled to be in communication with the processor 110. In some embodiments, the display 120 can be in the form of a touch sensitive screen, which can both display data and receive inputs from a user, for example, via the pointer.

The system 100 also includes a data store 140 coupled to be in communication with the processor 110. The data store 140 can be any suitable known memory with sufficient capacity for storing configured computer readable program code components 150, some or all of which are required to execute the functionality of the retinal image analysis system 100 as described in further detail hereinafter. The data store 140 stores configured computer readable program code components 150, some or all of which are retrieved and executed by the processor 110.

Embodiments of the retinal image analysis system 100 enable eye specialists or researchers to make use of retinal vessel biomarkers in a clinical setting or experimental setting, including assisting eye disease and systemic diagnosis, prediction and prevention. Eye disease including age-related macular degeneration (AMD), retinal artery occlusion, retinal vein occlusion, glaucoma, myopia and diabetic retinopathy (DR). Systemic disease including hypertension, diabetes mellitus, cardiovascular diseases (myocardial infarction, heart failure, atrial fibrillation, stroke), neurodegenerative diseases (dementia, Parkinson disease), chronic kidney disease.

Pre-Segmentation Image Quality Assessment

Figure 2:
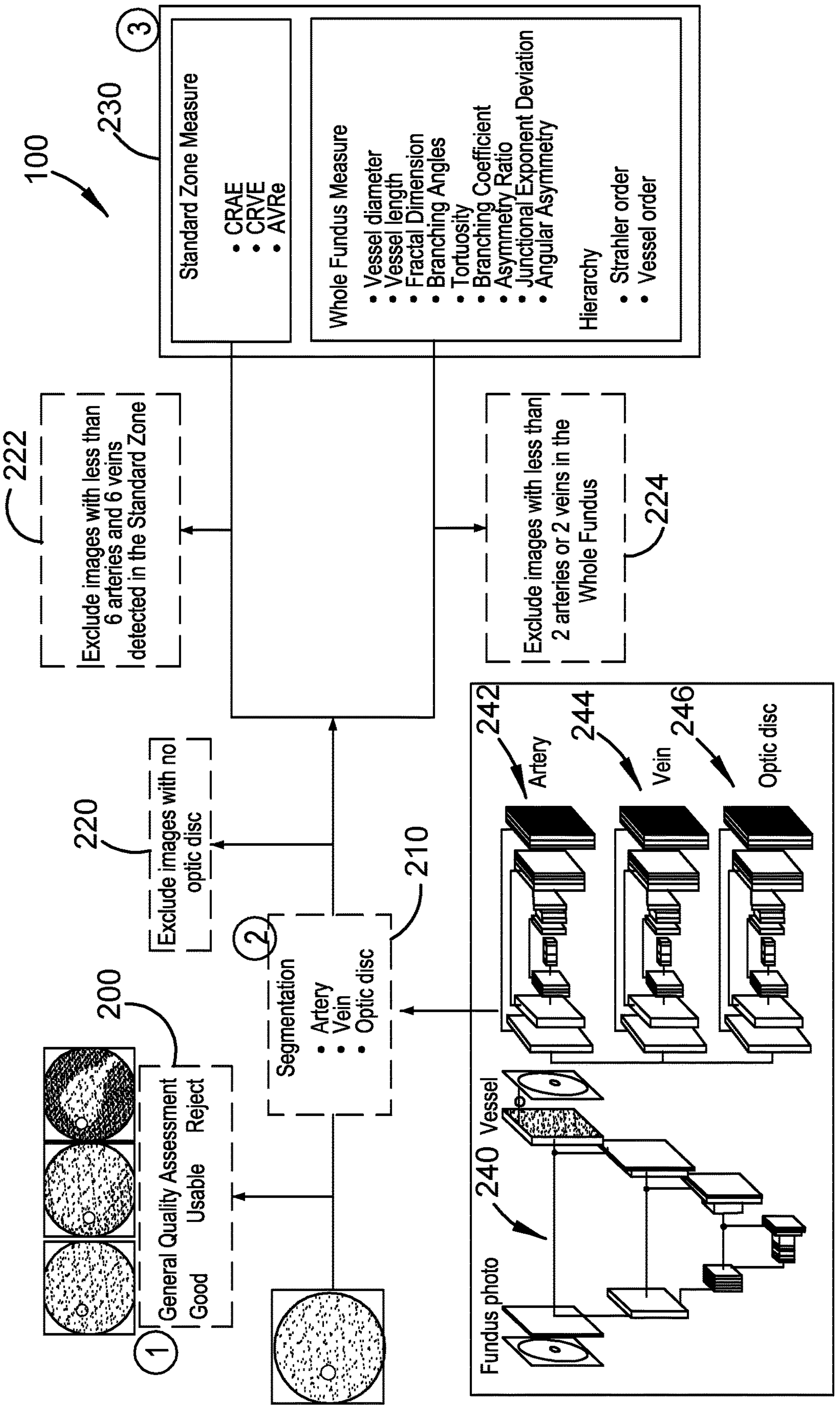
FIG. 2 depicts functional components of the fundus image analysis system of FIG. 1.

FIG. 2 depicts functional components of the retinal image analysis system 100, including a pre-segmentation image quality assessment module 200, a segmentation module 210, post-segmentation image quality assessment modules 220, 222 and 224 and a measurement module 230.

The input for fundus image analysis system 100 may be a fundus image, cropped to the field of view (FOV) and resized to preferably 512×512 pixels. The image quality assessment module 200 acts to assess overall image quality of the input fundus image before segmentation.

The module 200 is a convolutional neural network (CNN) trained from the EyeQ dataset, and acts to classify an input fundus image into three quality levels: 'good', 'usable', and 'reject'. Images with clear and identifiable main structures and lesions, but with some low-quality factors (blur, insufficient illumination, shadows) are classified as 'usable'.

Images with serious quality issues that are not reliably diagnosed by an ophthalmologist are classified as 'reject'. All other images are classified as 'good'.

The general quality assessment carried out by the image quality assessment module 200 is helpful for whole-retinal measures (where ideally every part of the retina should be visible) and offers operators of the retinal image analysis system 100 the flexibility to stratify their measurements in subsequent analysis, and investigate the influence of image quality on retinal vessel biomarkers and target diseases.

Segmentation

The segmentation module 210 generates artery, vein, and optic disc segmentation maps from fundus images determined to be 'good' and 'usable' by the image quality assessment module 200.

The image quality assessment module 200 is a convolutional neural network included four stacked lightweight U-Net branches, to enable simultaneous and efficient retinal artery, vein, and optic disc segmentation.

The trunk 240 of this multi-branch U-Net convolutional neural network generates an intermediate retinal vessel feature map, which is concatenated with the input image and divided into three separate branches 242, 244 and 246 respectively for retinal artery, vein, and optic disc segmentation.

Figure 3:
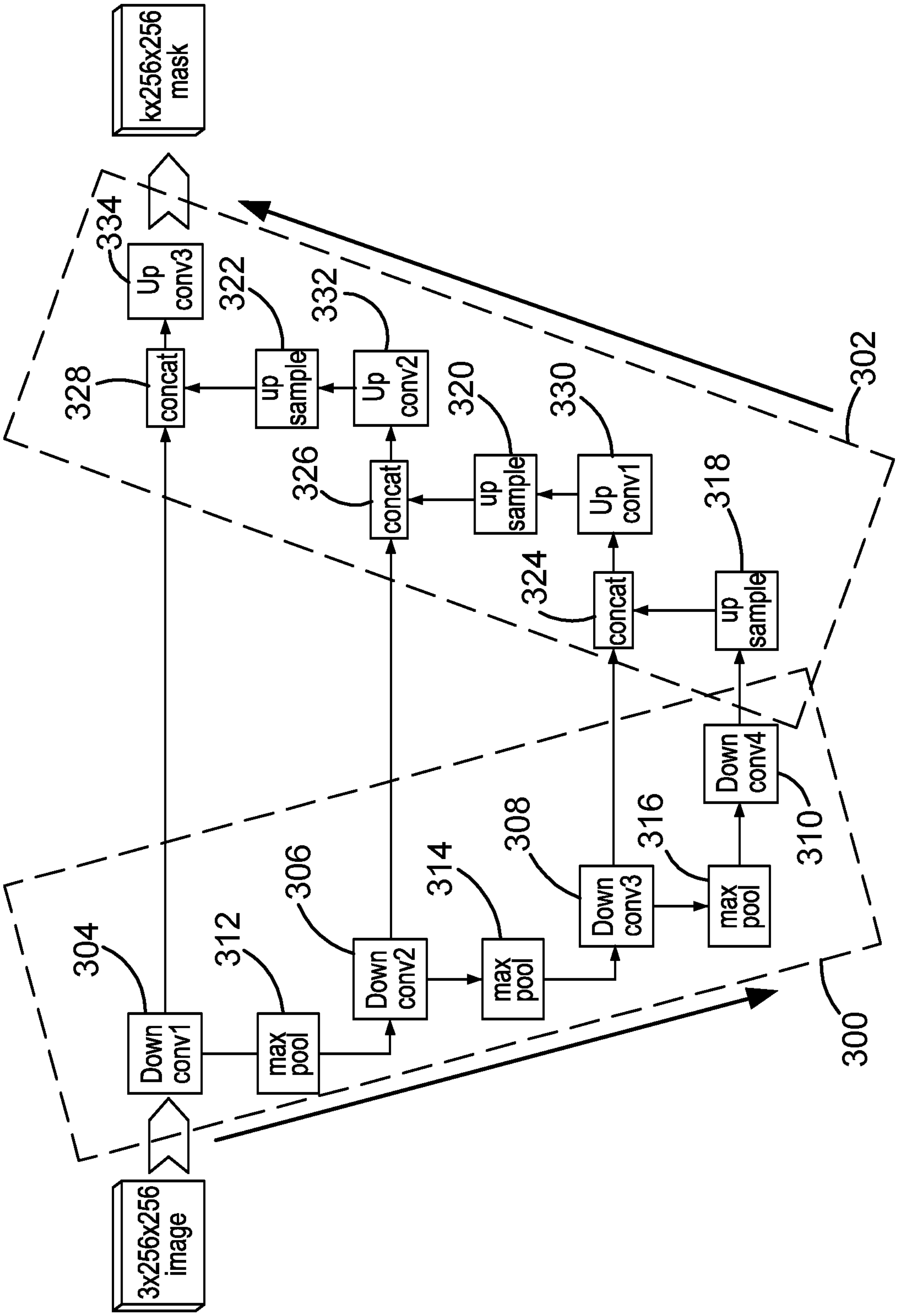
FIG. 3 depicts elements of a segmentation module forming one of the functional components depicted in FIG. 2.

As shown in FIG. 3, each U-net branch consists of a contracting path 300 and an expansive path 302, which gives it the u-shaped architecture. The contracting path 300 is a typical convolutional network that consists of repeated application of convolutions 304, 306, 308 and 310, each respectively followed by a rectified linear unit (ReLU) and a max pooling operation 312, 314 and 316. During the contraction, the spatial information is reduced while feature information is increased. The expansive pathway 302 combines the feature and spatial information through a sequence of up-sampling 318, 320 and 322, concatenations 324, 326 and 328 and up conversions 330, 332 and 334 with high-resolution features from the contracting path 300.

A first intermediate layer (the trunk 240) generates a segmentation map based on the whole retinal vessel map and concatenated it to the original fundus image. This first segmentation map is then used by the downstream network branches as targeted auxiliary information, to focus more on targeted areas of the image.

Post-Segmentation Image Quality Assessment

A second quality assessment is performed after segmentation by post-segmentation image quality assessment modules 220, 222 and 224. Images with the following conditions were excluded: no detectable optic disc; less than six arteries and six veins detectable in the Standard zone; or less than two arteries and two veins detected in the whole fundus. Excluded images, the reason to their exclusion, and their available measurements were saved separately from the main measurements.

Measurement

Based on the segmentation maps, the measurement module 230 computes region-specific measurements within a standard zone (for example, 0.5-1.0 disc diameter away from the optic disc margin), as well as global physical or geometric measures for the whole fundus image.

The measurement module 230 measures retinal vessel morphology by using custom region-specific summarization and global physical/geometric parameters. For region-specific summarization, the vessel calibers are summarized as central retinal artery equivalent (CRAE) and central retinal vein equivalent (CRVE) from the 6 largest arteries and veins detected in the standard zone, based on a revised Knudtson-Parr-Hubbard formula. Artery to vein ratio from equivalents (AVRe) are generated by dividing CRAE by CRVE.

In one or more embodiments, the measurement module also computes hierarchical orders to enable subsequent stratification. Orders may be assigned for each segment, Strahler order and vessel.

For global physical/geometric parameters, vessels are converted by the measurement module 230 into segments separated by interruptions at the branching or crossing points. Short vessels less than 10 pixels in length are excluded from the analysis. Using methods similar to SIVA, the diameters (mean, standard deviation [SD]), arc length, chord length, length diameter ratio (LDR), tortuosity, branching angle (BA), branching angle from edges (BA_edge), branching coefficient (BC), angular asymmetry (AA), asymmetry ratio (AR), junctional exponent deviation (JED), fractal dimension (FD) are measured and computed by the measurement module 230.

Graphic Representation

The vessel orders and Strahler orders of each segment are built by the measurement module 230 using graphical a representation for display by the display 120, resulting in a series of hierarchical nodes and edges. In summary, 16 basic parameters are included.

Figure 4:
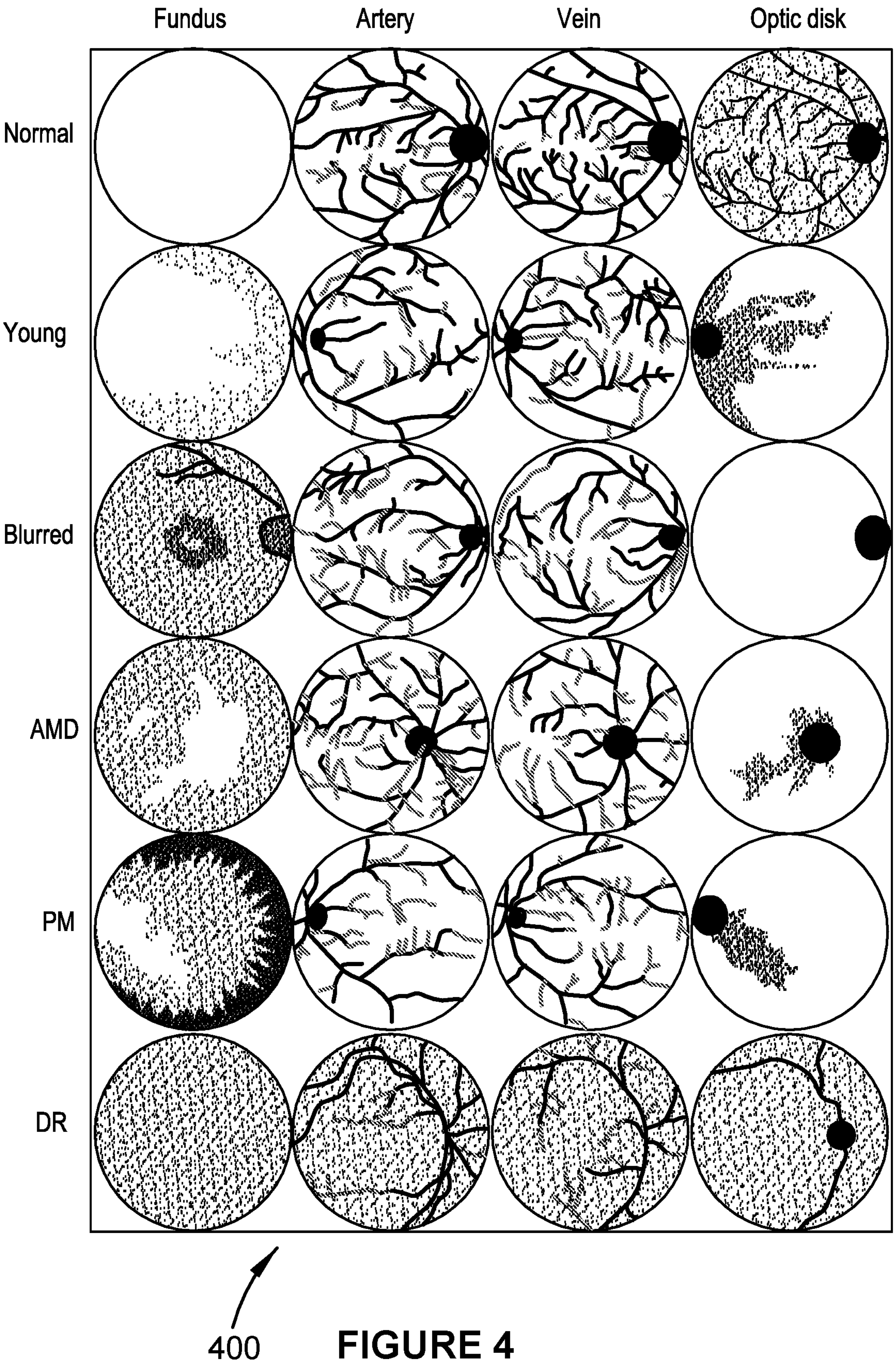
FIG. 4 is an illustration showing the representative examples of segmentation results of the segmentation module forming part of the fundus image analysis system of FIG. 1 versus human labeling.

FIG. 4 depicts representative examples 400 of segmentation results of the segmentation module of the fundus image analysis system 100 versus human labeling. Different conditions are illustrated, including a normal fundus, fundus image from young participants with prominent retinal nerve fiber layer reflections, blurred image from older participants, fundus with AMD, PM, and severe DR. In these representative examples:

a) Blue pixels indicate negative disagreements (pixels that were manually labeled but missed by the model);
b) Red pixels indicate positive disagreements (pixels identified by the model but missed by manual labeling); and
c) Green pixels indicate pixels with consistent segmentation between model and manual labeling. AMD, age-related macular degeneration; PM, pathologic myopia; DR, diabetic retinopathy.

The visualization of overlaid manual-predicted segmentation indicates that model predictions performed by the fundus image analysis system 100 outperform manual labeling, especially for small vessels that human graders often missed. For challenging cases, including images from young participants with highly reflective retinal nerve fiber layers, elderly participants with blurred retinal images, or retinal images with existing eye diseases, the algorithm provided segmentations more accurately than human graders.

Figure 5:
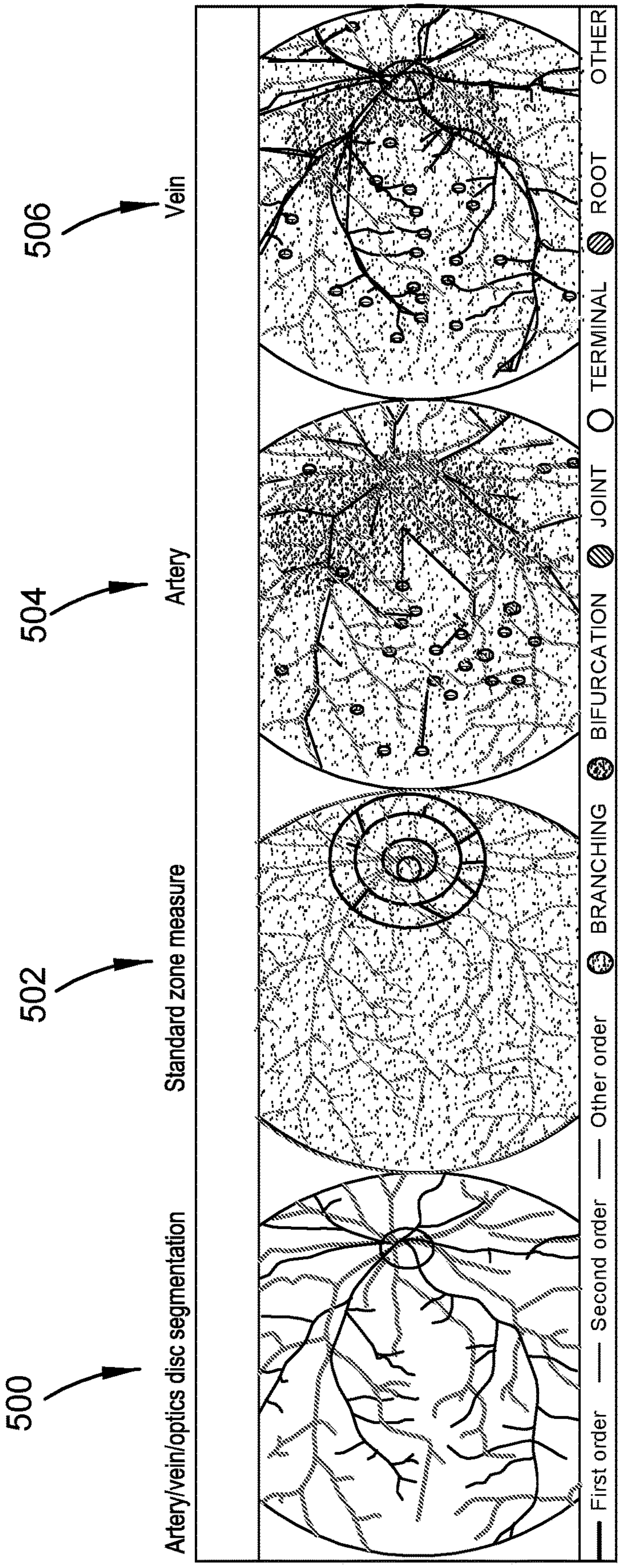
FIG. 5 is an illustration showing the examples of output images displayed by the fundus image analysis system of FIG. 1.

FIG. 5 is an illustration showing the examples of the fundus image analysis system 100 output. From left to right: artery, vein, and optic disc segmentation; parameters measured in the standard zone; parameters measured in the whole fundus for artery and vein, respectively. Measures are demonstrated and plotted visually. Users can examine the performance of each functional part throughout the analysis.

Images 500 to 506 (from left to right) are shown on the display 120 during operation of the system 100 and respectively depict a segmentation map of the artery, vein and optic disc. Based on the segmentation, the measurement module 230 detects the optic disc location and size, separates out a Standard Zone region (1.5 disc diameter to 1 disc diameter from the optic disc center) and detect arteries and veins.

The arteries and veins are sorted by their diameter. When 6 vessels are detected for both arteries and veins, CRAE and CRVE will be calculated and AVR (CRAE/CRVE) will be plotted on the second image 502. The third image 504 and fourth image 506 show vessel skeleton tracing and vessel graph building for arteries and veins respectively. Vessels with different orders (first, second and other) are colored in yellow, white and gray. Different nodes (root, bifurcation and branching) are colored in green, red and orange. Strahler orders are also displayed on nodes. The segment-level measurements are also calculated during vessel tracing.

The invention claimed is:

1. A fundus image analysis system including:
- a pre-segmentation image quality assessment module for
  - receiving a fundus input image, and
  - performing overall retinal image quality assessment and measurement quality assessment on the fundus input image;
- a segmentation module for segmenting retinal vessel, artery, vein and optic disc to produce segmentation maps from the fundus input image; and
- a measurement module for computing
  - region specific measurements within a standard zone within the fundus input image, and
  - global physical or geometric measures of the whole fundus input image.

2. The fundus image analysis system according to claim 1, wherein the segmentation module has a four stacked light-weight U-Net architecture, with a retinal vessel segmentation root and artery, vein and optical disc segmentation branches.

3. The fundus image analysis system according to claim 2, wherein the retinal vessel map generated by the retinal vessel segmentation root is used to guide subsequent artery, vein and optical disc segmentation.

4. The fundus image analysis system according to claim 3, wherein:
- the retinal vessel segmentation root
  - receives a fundus input image and
  - generates a vessel segmentation map; and
- the artery, vein and optical disc segmentation branches
  - receive the vessel segmentation map,
  - concatenate the vessel segmentation map to the fundus input image and
  - simultaneously generate artery, vein and optic disc segmentations from the concatenated vessel segmentation map and fundus input image.

5. The fundus image analysis system according to claim 1, and further including:
- a post-segmentation image quality assessment module for excluding selected images from subsequent measurement.

6. The fundus image analysis system according to claim 5, wherein the selected images are excluded on any one or more of the following criteria: no detectable optic disc; less than six arteries and six veins detectable in the standard zone; or less than two arteries and two veins detected in the whole fundus input image.

7. The fundus image analysis system according to claim 1, wherein the measurement module computes region specific measurements within a standard zone of 0.5-1.0 disc diameters away from an optic disc margin within the fundus input image.

8. The fundus image analysis system according to claim 7, wherein the measurement module measures a central retinal artery equivalent (CRAE) and central retinal vein equivalent (CRVE) from largest arteries and veins detected in the standard zone.

9. The fundus image analysis system according to either one of claim 7, wherein the measurement module converts vessels into segments separated by interruptions at the branching or crossing points, and measures one or more of diameter, arc length, chord length, length diameter ratio (LDR), tortuosity, branching angle (BA), branching angle from edges (BA_edge), branching coefficient (BC), angular asymmetry (AA), asymmetry ratio (AR), junctional exponent deviation (JED), and fractal dimension (FD) of the segments.

10. The fundus image analysis system according to claim 1, wherein the measurement module also computes hierarchical orders to enable subsequent stratification.

11. The fundus image analysis system according to claim 10, wherein orders are assigned for each segment, Strahler order and vessel.

12. A method of analysing a fundus image including the steps of:
- at a pre-segmentation image quality assessment module,
  - receiving a fundus input image, and
  - performing overall retinal image quality assessment and measurement quality assessment on the fundus input image;
- at a segmentation module, segmenting retinal vessel, artery, vein and optic disc to produce segmentation maps from the fundus input image; and
- at a measurement module, computing
  - region specific measurements within a standard zone within the fundus input image, and
  - global physical or geometric measures of the whole fundus input image.

13. The method according to claim 12, wherein the segmentation module has a four stacked light-weight U-Net architecture, with a retinal vessel segmentation root and artery, vein and optical disc segmentation branches.

14. The method according to claim 13, and further including the step of using the retinal vessel map generated by the retinal vessel segmentation root to guide subsequent artery, vein and optical disc segmentation.

15. The method according to claim 14, wherein:
- the retinal vessel segmentation root
  - receives a fundus input image and
  - generates a vessel segmentation map; and
- the artery, vein and optical disc segmentation branches
  - receive the vessel segmentation map,
  - concatenate the vessel segmentation map to the fundus input image and
  - simultaneously generate artery, vein and optic disc segmentations from the concatenated vessel segmentation map and fundus input image.

16. The method according to claim 12, and further including:
- at a post-segmentation image quality assessment module, excluding selected images from subsequent measurement.

17. The method according to claim 16, and further including:
- excluding the selected images on any one or more of the following criteria: no detectable optic disc; less than six arteries and six veins detectable in the standard zone; or less than two arteries and two veins detected in the whole fundus input image.

18. The method according to claim 12, and further including:

at the measurement module, computing region specific measurements within a standard zone of 0.5-1.0 disc diameters away from an optic disc margin within the fundus input image.

19. The method according to claim 18, and further including:

at the measurement module, measuring a central retinal artery equivalent (CRAE) and central retinal vein equivalent (CRVE) from largest arteries and veins detected in the standard zone.

20. The method according to claim 12, and further including, at the measurement module, computing hierarchical orders to enable subsequent stratification.

* * * * *